United States Patent [19]

Omid et al.

[11] Patent Number: 4,701,205

[45] Date of Patent: Oct. 20, 1987

[54] CHEMICAL TOBACCO SUCKER CONTROL

[75] Inventors: Ahmad Omid, Walnut Creek; Pawan K. Bassi, Benicia, both of Calif.

[73] Assignee: Chevron Research Company, San Francisco, Calif.

[21] Appl. No.: 854,448

[22] Filed: Apr. 21, 1986

[51] Int. Cl.[4] ............................................ A01N 31/04
[52] U.S. Cl. ....................................................... 71/78
[58] Field of Search ............................................ 71/78

[56] References Cited

U.S. PATENT DOCUMENTS 4,440,566  4/1984  Nuo .......................................... 71/98

Primary Examiner—Catherine L. Mills
Attorney, Agent, or Firm—S. R. LaPaglia; R. C. Gaffney; L. S. Squires

[57] ABSTRACT

Methods and compositions for controlling tobacco suckers, which comprise administering an effective amount of certain 2-[-1-(3-chloroallyloxyamino)ethylidene]-5-(2-substituted thioalkylidene)-cyclohexane-1,3-dione derivatives to said tobacco plants or their growth medium.

9 Claims, No Drawings

CHEMICAL TOBACCO SUCKER CONTROL

BACKGROUND OF THE INVENTION

This invention relates to the chemical control of tobacco suckers (i.e., axillary buds) via the application of certain trans-2-[1-(3-chloroallyloxy-amino)ethylidene]-5-(substituted thioalkylidene)-cyclohexane-1,3-dione derivatives.

Tobacco crop management requires that the terminal growing meristem be removed so that the number of usable leaves and their quality can be optimized. The removal of the terminal meristem, a process called topping, leads to the rapid development of lateral buds. These lateral buds are known as suckers. For maximum yield, the suckers have to be removed either manually or inhibited by chemical means. A further discussion on the growth and control of tobacco suckers can be found on pages 71–81 of Plant Growth Regulating Chemicals Vol. II, Ed. L. G. Nickell, CRC PRESS (1983).

In the chemical control of tobacco suckers, it is important that the chemical operates systemically; i..e, it should inhibit sucker development even when applied to other parts of the tobacco plant. This is important because in field-grown tobacco, the axillary buds, or suckers, are hidden in large leaf whorls. Thus, it is very difficult to apply the chemical spray such that it will directly contact the axillary buds. However, if the chemical operates systemically, it can be effectively applied to the leaves of the tobacco plant or even as a soil drench.

The most commonly used chemical for tobacco sucker control is maleic hydrazide. This systemic inhibitor, though effective, is not without its problems. Treatment with maleic hydrazide tends to leave undesirably high levels of residues in the leaves.

U.S. Pat. No. 4,440,566, issued Apr. 3, 1984, disclosed compounds having the formula:

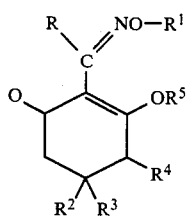

wherein R is most preferably alkyl of 3 to 3 carbon atoms, most preferably ethyl or propyl;

$R^1$ is most preferably 3-trans-chloroallyl or 4-chlorobenzyl;

$R^2$ and $R^3$ are preferably each alkyl of 1 to 3 carbon atoms or one of $R^2$ or $R^3$ is hydrogen and the other is alkylthioalkyl having 2 through 8 carbon atoms, most preferably $R^2$ and $R^3$ are each methyl or one of $R^2$ or $R^3$ is hydrogen and the other is 2-ethylthiopropyl.

This patent teaches that these compounds exhibit herbicidal activity against grasses and are safe with respect to broadleaf crops and also may be employed to prevent or retard the growth of lateral buds in plants and to promote the thinning out of fruit in various fruit trees.

SUMMARY OF THE INVENTION

It has now been discovered that certain of the compounds encompassed within U.S. Pat. No. 4,440,566, exhibit a surprising ability to control (inhibit) tobacco sucker growth which is unique to this sub-class of compounds. Such compounds are those having the formula:

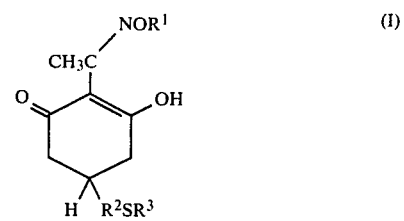

wherein $R^1$ is 3-transchloroallyl;

$R^2$ is alkylidene having 1 to 4 carbon atoms; and $R^3$ is alkyl having 1 to 4 carbon atoms or phenyl; and compatible salts thereof.

As is well recognized, compounds of the nature of Formula (I) exist as tautomers. The compounds also may have one or more asymmetric carbon atoms and thus can also exist as optical isomers. The above formula is intended to encompass the respective tautomeric forms as well as the individual optical isomers as well as mixtures thereof and the respective tautomers and optical isomers as well as mixtures thereof are encompassed within the invention.

In a further aspect the invention provides a tobacco axillary bud controlling composition comprising a compatible carrier and a tobacco axillary bud controlling effective amount of the compound(s) of Formula I or compatible salts thereof or mixtures thereof.

The invention will be further described hereinbelow.

FURTHER DESCRIPTION OF THE INVENTION AND THE PREFERRED EMBODIMENTS

The preferred compounds for controlling tobacco suckers (i.e., axillary buds) are those wherein $R^2$ is alkylene having 2 or 3 carbon atoms and $R^3$ is alkyl having 1 to 3 carbon atoms. More preferably $—R^2SR^3$ is selected from the group of 2-ethylthiopropyl (i.e., $—CH_2CH(CH_3)$ $SCH_2CH_3$); 2-methylthiopropyl (i.e., $—CH_2CH(CH_3)SCH_3$) and 2-propylthioethyl (i.e., $—CH_2CH_2SCH_2CH_2CH_3$).

Typically, the compounds are applied at application rates of 0.1 to 3.2 kilograms per hectare ("Kg/ha") preferably 0.4 to 2 Kg/ha. Best results are typically obtained using application rates of about from 0.8 to 1.6 Kg/ha. Mixtures of the compounds of Formula I can also be used. Optimum results may vary with the particular compound or compounds of Formula I used and the particular species of tobacco but can be obtained by routine experimentation. At high dosage rates (e.g., 5 kg/ha or above) certain of the compounds exhibit phytotoxicity with respect to certain broadleaf plants as well as grasses. Thus, high dosage rates should be avoided.

As noted above, it is conventional to remove the terminal growing meristem of the tobacco plant in order to optimize the number and quality of usable leaves. In accordance, with the practice of the present invention, it is preferable to apply the compounds of Formula I or their salts within two days, more preferably a day after removal of the terminal growing meristem. The compounds can be applied directly to the plants or to the soil. Most typically the compound is applied as a solution or liquid emulsion.

Although in theory the compounds can be applied undiluted, in actual practice they are generally applied as a composition of formulation, comprising an effective amount of the compound(s) of Formula I or their salts and an acceptable carrier. An acceptable or compatible carrier (agriculturally acceptable carrier) is one which does not significantly adversely affect the desired biological effect achieved by the active compounds, save to dilute it. The compositions can be prepared, both for direct application and also a concentrate designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents or carriers which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils.

The composition can also contain various compatible adjuvants, stabilizers, conditioners, insecticides, fungicides.

One convenient concentrate formulation which can be used comprises 20 to 30 by weight percent of the compound(s) of Formula I or salts thereof, of the invention, 2 to 4% by weight percent of an emulsifier, for example, alkylarylsulfonates, e.g., calcium alkylbenzene sulfonates, octylphenolethoxylate, polyoxyethylenealkylaryl, etc., or mixtures thereof, and about 66 to 76% organic solvent, for example, petroleum hydrocarbon and aromatics, e.g., xylene, kerosene, etc. For example, one suitable concentrate formulation which can be used comprises about 25 wt.% of the active compound; about 72 wt.% of a xylene base solvent sold under the Trademark "HiSol 10" by Ashland Oil Company, as the solvent and about 3 wt.% of mixture of alkylarylsulfonates and polyoxyethylenealkylaryl sold under the Trademark "Atlox 3454F" as the emulsifier.

The concentrate can be mixed with water, optionally containing a crop oil, prior to application and applied as a water emulsion, optionally containing about 0.125 to 2 wt. % of a crop oil, for example, soybean oils, and paraffinic oils and olefinic oils and/or surfactant. Conveniently, the composition is applied as a water emulsion spray containing about 0.01 to 0.32 wt. %, preferably 0.04 to 0.16 wt. % of the compound (s) of Formula I or salts thereof; about 0.001–0.0625 wt. % of an emulsifier; about 0.08–3.3 wt. % of an organic solvent and about 95 to 99 wt. % water and optionally 0.125 to 2 wt.% crop oil. The spray composition can be conveniently prepared by mixing the concentrate formulation with about ¼ to ½ the desired amount of water. Then admixing the crop oil, if used, and then adding the remaining amount of water. If no crop oil or additional surfactant is used, then the water and concentrate formulation are simply admixed together.

The compound of Formula (I) can be conveniently prepared by the following schematically represented process:

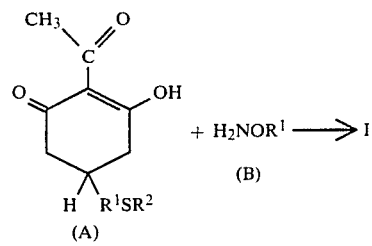

wherein $R^1$, $R^2$ and $R^3$ are as defined hereinbelow.

This process can be conveniently effected by contacting Compound (A) with 3-trans-chloroallyloxyamine (B), preferably in an inert organic solvent.

Typically, this process is conducted at temperatures in the range of about from 0° to 80° C., preferably about from 20° to 40° C., for about from 1 to 48 hours, preferably about from 4 to 12 hours, using about from 1 to 2, preferably 1.05 to 1.2 moles of 3-trans-chloroallyloxyamine (B) per mole of Compound (A). Suitable inert organic solvents which can be used include, for example, lower alkanols, e.g., methanol, ethanol, ethers, e.g., ethyl ether; methylene chloride. Two-phase water and immiscible organic solvent (e.g., hexane), and the like, and compatible mixtures thereof can also be used.

Trans-chloroallyloxyamine is a known compound and can be prepared via known procedures, such as, for example, described in U.S. Pat. No. 4,440,566. A hydrochloride salt of trans-chloroallyloxyamine can be conveniently used by neutralizing the salt with an alkali metal alkoxide, in situ.

The starting materials of Formula (A) can be prepared via the general procedure described in U.S. Pat. No. 4,440,566 and also in commonly assigned U.S. application Ser. No. 655,776, filed Sept. 27, 1984.

The compatible salts of Formula (I) can be prepared by conventional procedures, for example, via the reaction of the compound of Formula I with a base, such as, for example, sodium hydroxide, potassium hydroxide and the like, having the desired cation. Additional variations in the salt cation can also be effected via ion exchange with an ion exchange resin having the desired cation.

General Process Conditions

The reaction product can be recovered from its reaction product mixture by any suitable separation and purification procedure, such as, for example, chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where typical isomer mixtures are obtained, the respective optical isomers can be obtained by conventional resolution procedures. Geometric isomers can be separated by conventional separation procedures which depend upon differences in physical properties between the geometric isomers. However, it is generally preferable to use the desired isomeric starting material in the reaction.

Definitions

As used herein the following terms have the following meanings unless expressly stated to the contrary:

The term "alkyl" includes both straight chain and branched chain alkyl groups.

The term "alkylidene" includes both straight chain and branched chain alkylidene groups and includes, for example, groups having the formula

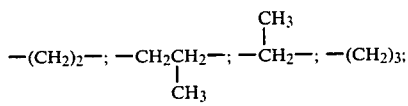

and the like.

The term "compatible salts" refers to salts which do not significantly adversely alter the herbicidal properties of the parent compound. Suitable salts include cation salts such as, for example, the cation salts of lithium, sodium, potassium, alkali earth metals, copper, zinc, ammonia, quaternary ammonium salts, and the like.

The term "room temperature" or "ambient temperature" refers to about 20°-25° C.

A further understanding of the invention can be had in the following non-limiting Preparation(s) and Example(s). Wherein, unless expressly stated to the contrary, all temperatures and temperature ranges refer to the Centigrade system and the term "ambient" or "room temperature" refers to about 20°-25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume.

EXAMPLES

Example 1

Trans-2-[1-(3-chloroallyloxyamino)-ethylidene]-5-(2-ethylthiopropyl)-cyclohexane-1,3-dione In this example, 29.5 g (0.1151 mol) of 2-acetyl-5-(2-ethylthiopropyl)cyclohexane-1,3-dione; 1.7 g (0.0277 mol) of acetic acid, and 19.7 g (0.1369 mol) of 3-trans-chloroallyloxyamine in 62 ml of water were admixed to 37 ml of hexane. Aqueous 5 wt. % sodium hydroxide was slowly added dropwise over about 15 minutes until 5.5 g (0.1369 m+small excess) of sodium hydroxide had been added yielding a reaction mixture pH of about 6. The mixture was heated to and maintained at 40° C. for 2½ hours and then cooled to room temperature. The organic (i.e., hexane) phase was separated and washed with 16 ml of aqueous 5 wt. % hydrochloric acid and then aqueous 6.25 wt. % sodium hydroxide added until pH12. The aqueous phase was separated and admixed with 35 ml of hexane at about 0° C. (ice bath) and the pH adjusted to 5 by the dropwise addition of aqueous 36 wt. % hydrochloric acid over an ice bath. A few mls of methylene chloride was then added. The organic phase was separated, dried over magnesium sulfate and then concentrated by evaporation affording 35.2 g of a crude product as an oil. The crude product was purified by column chromatography over silica gel eluting with hexane:methylene chloride mixtures affording 17.4 g of the purified title compound also as an oil. Elemental analysis carbon calculated 55.56%, found 54.43%; Hydrogen calculated 6.99%, found 6.53%; Nitrogen 4.05%, found 4.31%.

Example 2

Sodium 2-[1-(3-trans-chloroallyloxyimino)ethyl-3-oxo-5-(2-ethylthiopropyl)cyclohex-1-en-1-olate This example illustrates a procedure which can be used to prepare the title compound.

A solution containing 0.01 mole of sodium hydroxide dissolved in 2 ml of water is added to a solution containing 0.01 mole of 2-[1-(3-trans-chloroallyloxyamino)ethylidene-5-(2-ethylthiopropyl)-cyclohexane 1,3-dione at room temperature. After the reaction is completed, the solvents are evaporated off under vacuum affording the 1-hydroxy sodium salt of 2-[1-(3-trans-chloroallyloxyamino)ethylidene-3-oxo-5-(2-ethylthiopropyl)cyclohex-1-en-1-ol.

Example 3

In this example, the title compound of Example 1 (i.e., 2-[1-(3-trans-chloroallyloxyamino)ethylidene]-5-(2-ethylthiopropyl)cyclohexane-1,3-dione was tested side-by-side with 2-[1-(3-trans-chloroallyloxyamino)-butylidene]-5-(2-ethylthio-propyl)-cyclohexane-1,3-dione for their ability to control (retard or prevent) lateral axillary buds in tobacco plants.

These tests were conducted using the following procedure.

Twenty-four hours before treatment, the tobacco plants are "topped", removing the top 15 cm of the plant. Any plants which are tending to lean or bend in the pot were staked, and all pots labeled. Three to five replicates were used per treatment. A 5% wt. stock solution of each test compound dissolved in acetone containing a small amount of non-ionic emulsifier was prepared. The stock solution was appropriately diluted with deionized water containing 0.625 g of emulsifier per liter of water, to the desired spray solution concentration. (The spray solution concentration (dosage rate and species of tobacco plant used are indicated in the following tables.)

Application

Plants were sprayed to point of run-off with a pressure atomizer, making sure that the stem, leaf axils, and leaves were all wet thoroughly with the solution. 30 to 35 ml of solution were used per plant. This was checked by recording volume of solution in sprayer reservoir before and after treatment. After spraying, the plants were incubated for 18 to 23 days in a greenhouse maintained at 70°-80° F. using standing water capilliary irrigation. The plants were uniformly fertilized once per week with a standard house plant fertilizer. After the incubation period, the plants were evaluated at various times for sucker control. To make this evaluation, the axillary buds at the top three nodes (primary suckers) of each plant were compared to those of the check, and a visual estimation of percent inhibition was made wherein 0=no inhibition of axillary buds as compared with check and 100=no axillary buds at top three nodes. The growth of secondary suckers (buds at lower nodes) when present, were also measured.

In some instances, comparisons were also made on the basis of sucker length.

The results are reported as an average of the replicates used in each test. The results of these tests and the dosage rates, evaluation times, etc., used are indicated in the following tables.

TABLE I

Tobacco Sucker Control (Var. Glurk[1])

| Compound | ** Dosage[2] Concentration mg/l | Three Weeks After Treatment[3] Percent Bud Inhibition | Number of Usable Leaves |
|---|---|---|---|
| 1[4] | 1600 | 100 | 6.3 |
| 1 | 800 | 100 | 6.7 |
| 1 | 400 | 100 | 6.7 |
| C-1[5] | 1600 | 7 | 6.0 |
| C-1 | 800 | 0 | 7.7 |
| C-1 | 400 | 0 | 7.3 |
| Check | — | 0 | 7.0 |

| Compound | Dosage[2] Concentration mg/l | Six Weeks After Treatment[3] Percent Bud Inhibition Top two Nodes | Number of Secondary Suckers[6] | Total Sucker Length-cm[7] |
|---|---|---|---|---|
| 1 | 1600 | 100 | 0 | 0 |
| 1 | 800 | 100 | 1.3 | 7 |
| 1 | 400 | 100 | 2.3 | 24 |
| C-1 | 1600 | 0 | 0 | 0 |
| C-1 | 1600 | 0 | 0 | 0 |
| C-1 | 800 | 0 | 0 | 0 |
| C-1 | 400 | 0 | 0 | 0 |

TABLE I-continued

Tobacco Sucker Control (Var. Glurk[1])

| Check | — | 0 | 0 | 0 |
|---|---|---|---|---|

[1]Var. Glurk: *Nicotiana tabacum*
[2]Concentration of test compound in spray solution
[3]Weeks after spraying of tobacco plants with test compound
[4]Compound No. 1 = 2-[1-(3-trans-chloroallyloxyamino)ethylidene]-5-(2-ethylthiopropyl)cyclohexane-1,3-dione
[5]Compound No. C-1 = 2-[1-(3-trans-chloroallyloxyamino)butylidene]-5-(2-ethylthiopropyl)cyclohexane-1,3-dione
[6]i.e., Axillary buds at lower nodes
[7]Total length of all suckers on plant in cm
**At the spray volume and area used in the tests 1000 mg/l equals an application rate approximately 1 Kg/ha.

Example 4

In this example, the title compound of Example 1 was tested side-by-side with maleic hydrazide ("C-2") with respect to axillary bud control in two varities of tobacco plants. These tests were conducted following the same general procedure as described in Example 3 hereinabove using the dosage concentrations given in the tables hereinbelow.

TABLE 2

Tobacco Sucker Control

| Compound | Dosage[2] Concentration mg/l | Percent Bud Inhibition Top Two Nodes Var. Glurk[1] | Var. 12 × L8[8] |
|---|---|---|---|
| | | Three Weeks After Treatment[3] | |
| 1[4] | 800 | 100 | 95 |
| 1 | 400 | 100 | 93 |
| 1 | 200 | 100 | 95 |
| C-2[9] | 800 | 93 | 95 |
| C-2 | 400 | 88 | 23 |
| C-2 | 200 | 10 | 0 |
| Check | — | 0 | 0 |
| | | Six Weeks After Treatment[3] | |
| 1 | 800 | 100 | 96.8 |
| 1 | 400 | 100 | 96.9 |
| 1 | 200 | 100 | 86.3 |
| C-2 | 800 | 100 | 100 |
| C-2 | 400 | 100 | 54.1 |
| C-2 | 200 | 31.1 | 12.7 |
| Check | — | 0 | 0 |

[1]*Nicotiana tabacum*
[2]Concentration of test compound in spray solution; at volume and area used 1000 mg/l equals about 1 Kg/ha;
[3]Weeks after spraying of tobacco plants with test compound
[4]Compound No. 1 = 2-[1-(3-trans-chloroallyloxyamino)ethylidene]-5-(2-ethylthiopropyl)cyclohexane-1,3-dione
[8]*Nicotiana tabacum*
[9]Compound No. C-2 = Maleic hydrazide

TABLE 3

Tobacco Sucker Control Six Weeks After Treatment[3]

| | | Var. Glurk[1] | | Var. 12 × L8[8] | |
|---|---|---|---|---|---|
| Compound | Dosage[2] Concentration mg/l | Mean # of Nodes with Secondary Suckers | Mean Sucker Length (cm) | Mean # of Nodes with Secondary Suckers | Mean Sucker Length (cm) |
| 1[4,10] | 800 | 0.5* | 10.0 | 2.3* | 17.4 |
| 1 | 400 | 1.5 | 9.6 | 2.6 | 45.3 |
| 1 | 200 | 2.5 | 30.8 | 4.0 | 24.0 |
| C-2[9] | 800 | 2.5 | 31.0 | 5.3 | 25.8 |
| | 400 | 1.5 | 51.0** | 1.3 | 76.8 |
| | 200 | 0 | 0 | 0.3 | 3.0 |

TABLE 3-continued

| | | Tobacco Sucker Control Six Weeks After Treatment[3] | | | |
|---|---|---|---|---|---|
| | | Var. Glurk[1] | | Var. 12 × L8[8] | |
| Compound | Dosage[2] Concentration mg/l | Mean # of Nodes with Secondary Suckers | Mean Sucker Length (cm) | Mean # of Nodes with Secondary Suckers | Mean Sucker Length (cm) |
| Check | | | | | |

[1]Nicotiana tabacum
[2]Concentration of test compound in spray solution. At volume used in test 1000 mg/l equals approximately 1 Kg/ha
[3]Weeks after spraying of tobacco plants with test compound
[4]Compound No. 1 = 2-[1-(3-trans-chloroallyloxyamino)ethylidene]-5-(2-ethylthiopropyl)cyclohexane-1,3-dione
[8]Nicotiana tabacum
[9]Maleic hydrazide
[10]Mature leaves treated with Compound No. 1 were 25% phytotoxic in the Var. 12 × L8 species. This injury may cause some reduction in usefulness of the affected leaves.
*Note: Development of the primary suckers suppresses the growth of secondary suckers, resulting in few suckers. Also, generally, the fewer the secondary suckers, the greater their mean sucker length. Conversely, a compound which suppresses primary suckers is likely to show more secondary suckers than a compound which does not suppress primary suckers.

Example 5

In this example the effect of the title compound of Example 1 on leaf surface area was determined. These tests were conducted using the same general procedure described in Example 3, with the exception that two varieties of plants were used and that leave surface area was measured.

TABLE 4

| | | Tobacco Sucker Control | |
|---|---|---|---|
| | | Comparative Leaf Area (cm$^2$) Three After Treatment | |
| Compound | Rate[2] mg/l | Var. Glurk[1] 4 Pots | Var. 12 × L8[8] 4 Pots |
| 1[4] | 800 | 141.00 | 284.50 |
| 1 | 400 | 130.15 | 334.13 |
| 1 | 200 | 155.03 | 240.53 |
| 1 | 100 | 155.48 | 244.40 |
| Check | — | 128.88 | 228.28 |

[1]Nicotiana tabacum
[2]1000 mg/l equals approximately 1 Kg/ha
[4]Compound No. 1 = 2-[1-(3-trans-chloroallyloxyamino)ethylidene]-5-(2-ethylthiopropyl)cyclohexane-1,3-dione
[8]Nicotiana tabacum

Example 6

In this example, the title compound of Example 1 was tested side-by-side with maleic hydrazide for tobacco sucker control (inhibition), when applied as a soil drench and also when applied only to the leaves of the plant. The same general procedure as described in Example 3 was used with the exception that the test compound was applied only to the expanded leaves for foliage treatment (foliar paint) and the compound was drenched only on the soil in the pot for soil drench treatment. The average results of these tests are given in the following table, wherein 0=no inhibition and 100=complete inhibition, i.e., no axillary buds.

TABLE 5

| | Tobacco Sucker Control | | |
|---|---|---|---|
| | Three Weeks After Treatment Percent Bud Inhibition Top Three Nodes | | |
| Compound | Rate mg/l | Soil Drench (30 ml/pot) | Foliar Paint (Leaves Only) |
| 1 | 400 | 100 | 98 |
| C-2 | 400 | 79 | 15 |
| Check | — | 0 | 0 |

Compound Code
1 = 2-[1-(3-trans-chloroallyloxyamino)ethylidene]-5-(2-ethylthiopropyl)cyclohexane-1,3-dione
C-2 = maleic hydrazide
C-3 = butralin [i.e., 4-(1,1-dimethylethyl)-N—(1-methyl- TABLE 5-continued

| | Tobacco Sucker Control | | |
|---|---|---|---|
| | propyl)-2,6-dinitrobenzenamine] Six Weeks After Treatment Percent Bud Inhibition Top Three Nodes | | |
| Compound | Rate mg/l | Soil Drench (30 ml/pot) | Foliar Paint (Leaves Only) |
| 1 | 400 | 100 | 99$^a$ |
| C-2 | 400 | 84$^{a,b}$ | 0 |
| C-3 | 400 | 27 | 3 |

$^a$some suckers appearing at basal nodes
$^b$new growth deformed-strap shaped leaves From the above results, it can be seen that Compound 1 operates systemically and was highly effective when applied only to the leaves of the tobacco plant and also when applied as a soil drench. Maleic hydrazide also operates sytemically as indicated by the soil drench test but apparently does not translocate effectively from leaves to the sucker site. Butralin did not operate systemically and was ineffective when applied only to the leaves or as a soil drench.

Obviously, many modifications and variations of the invention described hereinabove and below can be made without departing from the essence and scope thereof.

What is claimed is:

1. A method for inhibiting the growth of axillary buds in tobacco plants which comprises applying to said tobacco plants or their growth medium an amount effective to inhibit the growth of axillary buds of a growth control agent selected from the group of compounds having the formula:

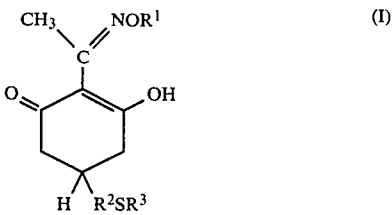

(I)

wherein R$^1$ is 3-trans-chloroallyl;
R$^2$ is alkylidene having 1 to 4 carbon atoms;
R$^3$ is alkyl having 1 to 4 carbon atoms or phenyl; compatible salts of the compounds of Formula I; and mixtures thereof.

2. The method of claim 1 wherein R$^2$ is alkylidene having 2 or 3 carbon atoms.

3. The method of claim 1 wherein R$^3$ is alkyl.

4. The method of claim 1 wherein $R^3$ is methyl, ethyl or propyl.

5. The method of claim 1 wherein $R^3$ is methyl, ethyl or propyl and $R^2$ is alkylidene having 2 or 3 carbon atoms.

6. The method of claim 1 wherein the group $-R^2SR^3$ is $-CH_2CH(CH_3)SCH_2CH_3$.

7. The method of claim 1 wherein the group $-R^2SR^3$ is $-CH_2CH(CH_3)SCH_3$.

8. The method of claim 1 wherein the group $-R^2SR^3$ is $-(CH_2)_2SCH_2CH_2CH_3$.

9. The method of claim 1 wherein said growth regulating agent is applied at a rate of about from 0.4 to 2 kg/ha.

* * * * *